United States Patent [19]

Lageson

[11] Patent Number: 5,300,051
[45] Date of Patent: Apr. 5, 1994

[54] URINARY CATHETER DEVICE

[76] Inventor: Catherine J. Lageson, 2140 N. 72nd St., Wauwatosa, Wis. 53213-1806

[21] Appl. No.: 27,651

[22] Filed: Mar. 8, 1993

[51] Int. Cl.$^5$ ............................................. A61F 5/44
[52] U.S. Cl. .................................. 604/330; 604/329; 128/761; 600/31
[58] Field of Search ........................ 604/329-331; 600/29-31, 38-40; 128/760, 761, 883-886; 4/144.1-144.4

[56] References Cited

U.S. PATENT DOCUMENTS

| | | | |
|---|---|---|---|
| 4,023,560 | 5/1977 | Cade et al. | 604/329 |
| 4,139,006 | 2/1979 | Corey | 128/761 |
| 4,846,819 | 7/1989 | Welch | 604/329 |
| 4,986,823 | 1/1991 | Anderson et al. | 604/329 |
| 5,007,894 | 4/1991 | Enhorning | 600/29 |

FOREIGN PATENT DOCUMENTS 0264258  4/1988  European Pat. Off. ............. 600/39

Primary Examiner—Randall L. Green
Assistant Examiner—Rob Clarke
Attorney, Agent, or Firm—Leon Gilden

[57] ABSTRACT

The organization is arranged to provide for a sterile spacing of the labia majora permitting retraction of the labia majora permitting ease of inserting a catheter device into the urethra. The organization is of a pentagonal configuration to anatomically accommodate the labia majora and to visualize the urethra.

3 Claims, 4 Drawing Sheets

URINARY CATHETER DEVICE

BACKGROUND OF THE INVENTION

1. Field of the Invention

The field of invention relates to catheter devices, and more particularly pertains to a new and improved urinary catheter device wherein the same is arranged to provide for the spacing of the labia majora for the combination use of a catheter device.

2. Description of the Prior Art

Various catheter devices such as indicated in the U.S. Pat. Nos. 4,571,241 and 4,710,169, as well as 4,575,371 are provided. The failings of the prior art have been heretofore the bacterial contamination relative to such procedures. Further, when patients are unavailed of placing their legs in a lithotomy position, such as due to obesity, the instant invention provides for a continuous pentagonal member formed of a durable resilient construction for insertion and spreading of the labia majora permitting the ease of use in a sterile manner of various catheter devices and in this respect, the present invention substantially fulfills this need.

SUMMARY OF THE INVENTION

In view of the foregoing disadvantages inherent in the known types of catheter tool structure now present in the prior art, the present invention provides a urinary catheter device wherein the same provides a resilient pentagonal member to accommodate positioning and conformity to the labia majora. As such, the general purpose of the present invention, which will be described subsequently in greater detail, is to provide a new and improved urinary catheter device which has all the advantages of the prior art catheter tool structure and none of the disadvantages.

To attain this, the present invention provides an organization arranged for a sterile spacing of the labia majora permitting retraction of the labia majora permitting ease of inserting a catheter device into the urethra. The organization is of a pentagonal configuration to anatomically accommodate the labia majora, labia minora, and urethral opening.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved urinary catheter device which has all the advantages of the prior art catheter tool structure and none of the disadvantages.

It is another object of the present invention to provide a new and improved urinary catheter device which may be easily and efficiently manufactured and marketed.

It is a further object of the present invention to provide a new and improved urinary catheter device which is of a durable and reliable construction.

An even further object of the present invention is to provide a new and improved urinary catheter device which is susceptible of a low cost of manufacture with regard to both materials and labor, and which accordingly is then susceptible of low prices of sale to the consuming public, thereby making such urinary catheter devices economically available to the buying public.

Still yet another object of the present invention is to provide a new and improved urinary catheter device which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
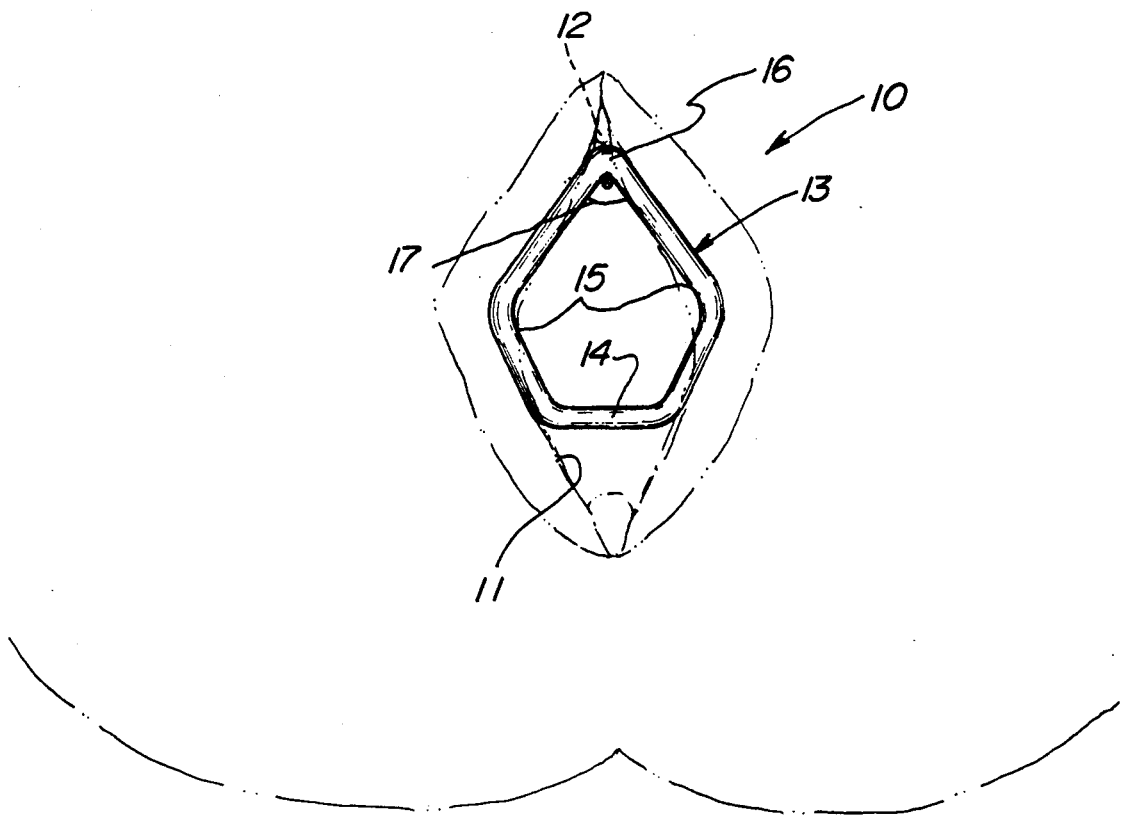
FIG. 1 is an orthographic view of the invention in use.
Figure 2:
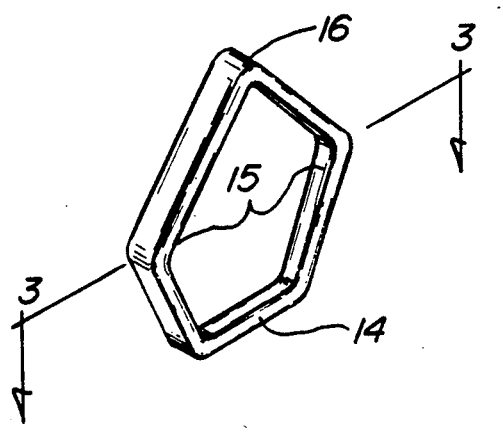
FIG. 2 is an isometric illustration of the invention.
Figure 3:
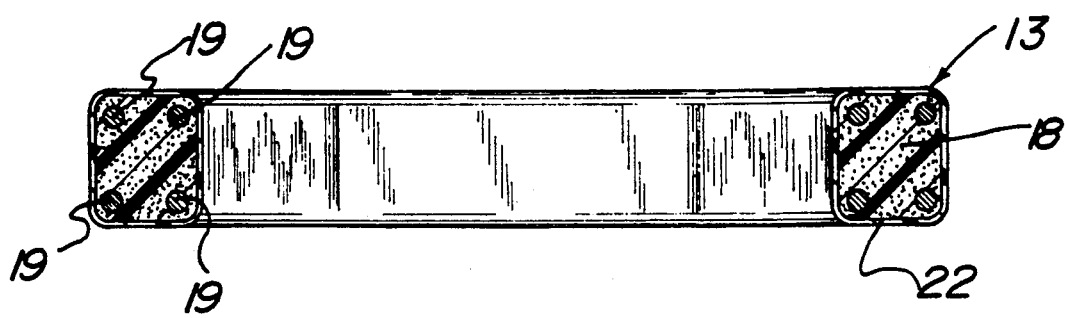
FIG. 3 is an orthographic view, taken along the lines 3—3 of FIG. 2 in the direction indicated by the arrows.

With reference now to the drawings, and in particular to FIGS. 1 to 8 thereof, a new and improved urinary catheter device embodying the principles and concepts of the present invention and generally designated by the reference numeral 10 will be described.

More specifically, the urinary catheter device 10 of the instant invention essentially comprises a pentagonal ring 13 arranged for positioning within the labia majora 11, as indicated in FIG. 1. The pentagonal ring includes a base leg 14 having opposed and facing V-shaped side legs 15 merging at an apex 16. The apex 16 is arranged for alignment with the labia majora apex 12, as indicated in FIG. 1, to accommodate the physiological characteristics of the anatomical member. The apex 16 is intermediate the merging of the side legs 15 defining an acute included angle 17 therebetween. The pentagonal ring 13 is formed of a polymeric resilient foam core 18 of a generally rectangular cross-sectional configuration for providing for enhanced positioning of the ring when positioned within the labia majora. The foam core includes continuous reinforcing rods 19 positioned within the foam core 18 in adjacency to each corner of the rectilinear cross-sectional configuration of the foam core 18 to provide for geometric integrity of the organization in use. A polymeric fluid impermeable skin 20 is mounted coextensively to the exterior surface of the ring 13 to provide for a shell containing the foam core 18 therewithin. In this manner, the organization provides for a non-slip member arranged for the spreading of the labia majora for the insertion of various catheter type tools, such as indicated in U.S. Pat. No. 4,710,169 incorporated herein by reference.

Figure 4:
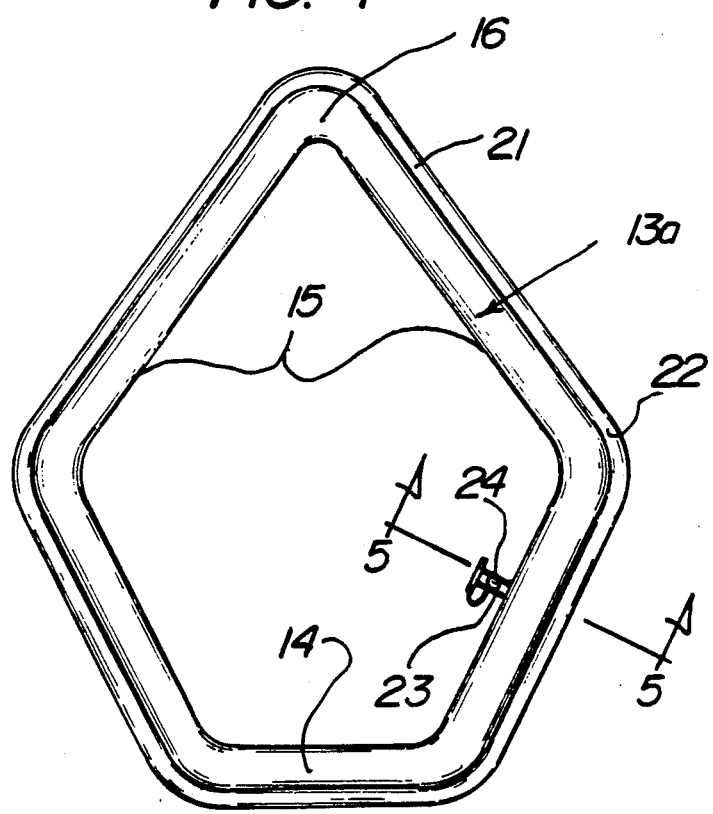
FIG. 4 is an orthographic view of a modified ring structure of the invention.
Figure 5:
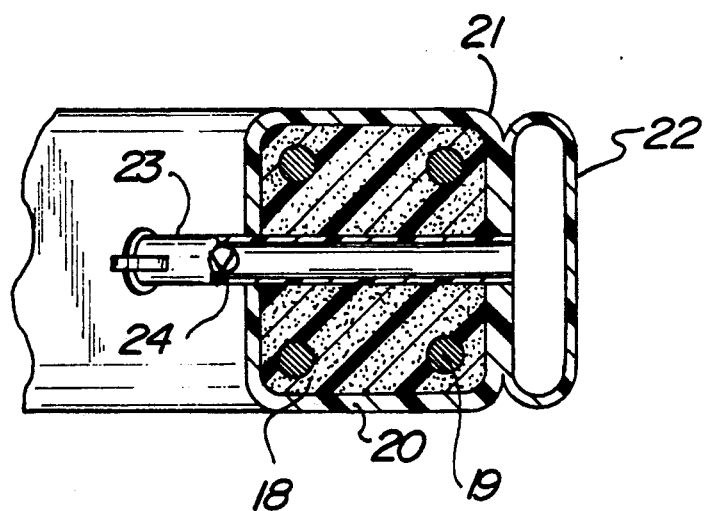
FIG. 5 is an orthographic view, taken along the lines 5—5 of FIG. 4 in the direction indicated by the arrows.
Figure 6:
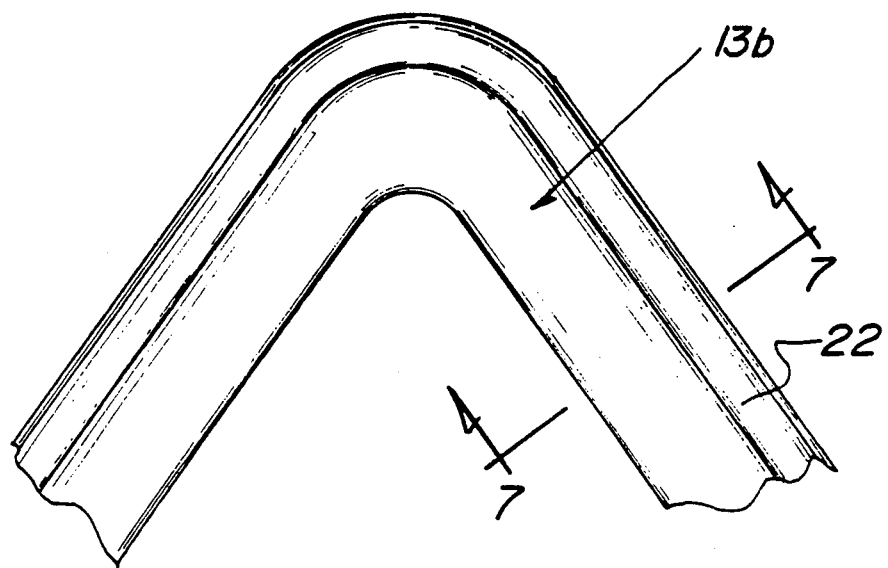
FIG. 6 is an orthographic partial view of a further modified ring structure of the invention.
Figure 7:
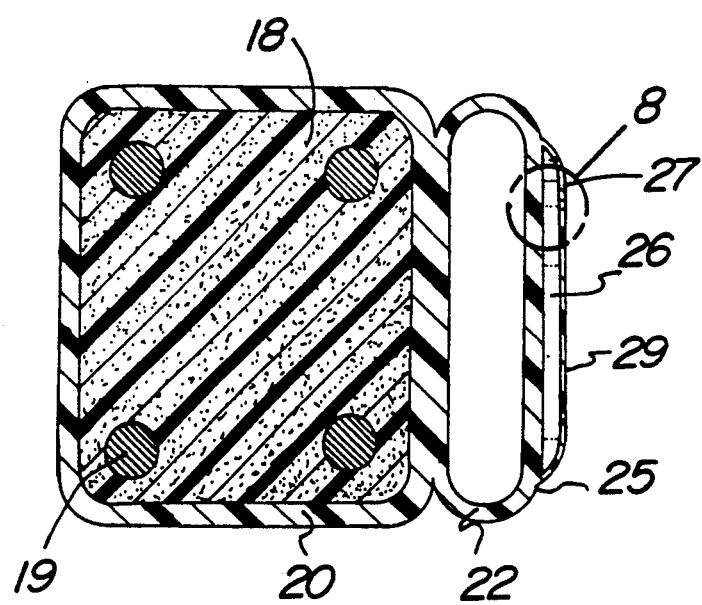
FIG. 7 is an orthographic view, taken along the lines 7—7 of FIG. 6 in the direction indicated by the arrows.
Figure 8:
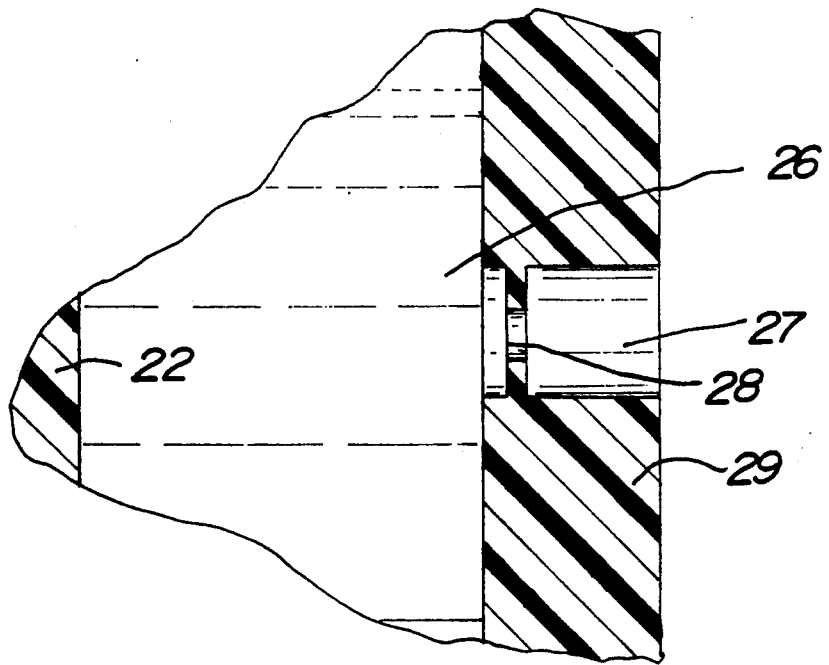
FIG. 8 is an enlarged orthographic view of section 8 as set forth in FIG. 7.

A modified pentagonal ring 13a is indicated in the FIG. 4, wherein the ring includes a ring outer periphery wall 21, having fixedly mounted thereon a pneumatic chamber 22 coextensive of the outer wall. The pneumatic chamber 22 includes an inflation tube 23 projecting interiorly of the ring, wherein the inflation tube includes an inflation tube valve 24 of any desired type to permit ease of inflation of the pneumatic chamber 22 to provide for enhanced tensioning of the ring and its non-slip mounting within the labia majora.

A further modified pentagonal ring structure 13b is indicated to include a fluid chamber 26 mounted to a pneumatic chamber outer periphery wall 25 of the pneumatic chamber 22. The fluid chamber 26 includes a fluid chamber fluid permeable outer wall 29 that is arranged coextensively with the fluid chamber 26 and the outer periphery wall 25 of the pneumatic chamber in a spaced relationship. At least one outlet port 27 is provided, having an orifice 28 within the outlet port to permit ease of filling of the fluid chamber, as well as insuring minimum projection of a lubricating fluid to the labia majora, as well as bactericide and the like, to minimize infection and abrasion in use of the organization.

Provisions will be made in the final design of the UCD to allow the device to be removed from the vulva and from around the catheter in order to maintain a sterile system from the indwelling cathether and the bag. A separable interlock connection (not shown) or severing of the ring is contemplated to perform this function.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A urinary catheter device, comprising, a pentagonal ring, the pentagonal ring including a base leg, having spaced V-shaped side legs extending from the base leg fixedly mounted to the base leg, with the V-shaped side legs merging together at an apex defining an acute angle therebetween for positioning and in communication with a labia majora apex of an individual, and the pentagonal ring includes a polymeric foam core of rectilinear cross-sectional configuration, and a plurality of reinforcing rods, wherein one of said reinforcing rods is positioned in adjacency to each corner of the rectilinear cross-sectional configuration of the pentagonal ring, and the polymeric foam core includes a polymeric fluid impermeable skin coextensively mounted in surrounding relationship relative to the foam core, and the pentagonal ring includes an inner wall spaced from an outer wall, the outer wall having a pneumatic chamber coextensive with the outer wall, and an inflation tube directed into the pneumatic chamber directed through the foam core, with the inflation tube having a valve therewithin permitting selective inflation of the pneumatic chamber.

2. A urinary catheter device as set forth in claim 1 wherein the pneumatic chamber includes a pneumatic chamber outer periphery wall, wherein the pneumatic chamber outer periphery wall is spaced from the pentagonal ring outer periphery wall, and a fluid chamber fixedly mounted to the pneumatic chamber outer periphery wall substantially coextensive therewith, wherein the fluid chamber includes a fluid chamber fluid permeable outer periphery wall spaced from the pneumatic chamber outer periphery wall to permit expressing of fluid therethrough, wherein the fluid chamber is arranged for accommodating a bactericide and lubricant fluid therewithin.

3. A urinary catheter device as set forth in claim 2 wherein the fluid chamber fluid permeable outer wall includes at least one outlet port, and the outlet port includes one orifice therewithin to permit selective filling of the fluid chamber and simultaneously permitting expressing of fluid through the orifice in the outlet port upon pressurizing the fluid chamber when positioned in the labia majora.

* * * * *